United States Patent
Ben-David et al.

(10) Patent No.: US 6,174,728 B1
(45) Date of Patent: Jan. 16, 2001

(54) CONTROL OR CALIBRATION STANDARD FOR USE WITH INSTRUMENTS FOR OPTICAL MEASUREMENT OF HEMOGLOBIN CONCENTRATION IN BLOOD SAMPLES

(75) Inventors: Daniel Ben-David, Alpharetta; Charles L. Laughinghouse, Cumming; James K. Tusa, Alpharetta, all of GA (US); Werner Ziegler, Graz (AT); Herbert Kroneis, Graz (AT); Ewald Jöbstl, Graz (AT)

(73) Assignee: AVL Medical Instruments AG, Schaffhausen (CH)

( * ) Notice: Under 35 U.S.C. 154(b), the term of this patent shall be extended for 0 days.

(21) Appl. No.: 09/054,461

(22) Filed: Apr. 3, 1998

(51) Int. Cl.⁷ ..................................................... G01N 31/00
(52) U.S. Cl. .................................. 436/16; 436/8; 436/10; 436/11; 436/15; 436/18; 436/66; 436/68; 436/74; 436/79; 702/19; 702/21
(58) Field of Search ................................... 436/8, 10, 11, 436/15, 16, 18, 63, 66, 68, 74, 79; 252/408.1; 73/1.01, 1.02, 1.03; 702/19, 21

(56) References Cited

U.S. PATENT DOCUMENTS

| | | | |
|---|---|---|---|
| 3,977,995 | * 8/1976 | Louderback et al. | 436/10 |
| 4,001,142 | * 1/1977 | Turner | 436/11 |
| 4,151,108 | * 4/1979 | Sorensen et al. | 436/11 |
| 4,279,775 | * 7/1981 | Louderback et al. | 436/11 |
| 4,299,728 | * 11/1981 | Cormier et al. | 436/11 |
| 4,469,792 | * 9/1984 | Simmonds et al. | 436/11 |
| 4,945,062 | 7/1990 | Chiang | 436/11 |
| 5,013,666 | * 5/1991 | Chiang | 436/11 |
| 5,185,263 | * 2/1993 | Kroneis et al. | 436/8 |
| 5,187,100 | 2/1993 | Matzviger et al. | 436/16 |
| 5,227,305 | * 7/1993 | Manzoni et al. | 436/19 |
| 5,308,767 | * 5/1994 | Terashima | 436/12 |
| 5,422,278 | * 6/1995 | Herring | 436/11 |
| 5,547,874 | 8/1996 | Terashima | 436/12 |
| 5,558,985 | * 9/1996 | Chiang et al. | 435/4 |
| 5,605,837 | 2/1997 | Karimi et al. | 436/14 |

FOREIGN PATENT DOCUMENTS

| | | |
|---|---|---|
| 0774655 | 5/1997 | (EP) . |
| 1129873 | 10/1968 | (GB) . |
| 2023287 | 12/1979 | (GB) . |
| 2308444 | * 6/1997 | (GB) . |
| 1301166 | 1/1989 | (JP) . |

OTHER PUBLICATIONS

Database WPI, Week 9003, Derwent Pub., AN 90–020045 of JP 01 301166A, dated Dec. 5, 1989.
Database WPI, week 8846, Derwent Pub., AN 88–328146 of JP 63 243879, dated Oct. 11, 1988.

* cited by examiner

Primary Examiner—Maureen M. Wallenhorst
(74) Attorney, Agent, or Firm—Dykema Gossett PLLC

(57) ABSTRACT

A control or calibration standard for use with instruments for the optical measurement of the hemoglobin content in blood samples, features scattering particles or beads dispersed in aqueous electrolyte solution. To prevent sedimentation of the beads during storage, they have a mean diameter of <0.6 $\mu$m, preferably about 0.3 $\mu$m, and a volume concentration of <1%, preferably <0.3%. To prevent long term agglomeration, a non-ionic surfactant with an added antioxidant can be included in the formulation.

25 Claims, No Drawings

CONTROL OR CALIBRATION STANDARD FOR USE WITH INSTRUMENTS FOR OPTICAL MEASUREMENT OF HEMOGLOBIN CONCENTRATION IN BLOOD SAMPLES

BACKGROUND OF THE INVENTION

The invention relates to a control or calibration standard for use with instruments for optical measurement of the hemoglobin concentration in blood samples, and which includes scattering particles dispersed in an aqueous electrolyte solution.

DESCRIPTION OF THE PRIOR ART

For calibration and quality control in medical instrumentation systems, in particular for determination of the concentrations of different blood components, it is essential to provide stable control and calibration standards of good storage stability, for calibrating such systems prior to measuring and/or for to quality control at certain intervals.

Known hemoglobin standards are based on a suspension of red blood cells and platelets in an electrolytic solution, for example, which are used in determining the number of particles, hematocrit, and hemoglobin content. The standard is prepared using stabilized cell components of the blood. Such a standard is described in GB 2023287 A, for instance.

It is further known in the art to prepare hemoglobin standards from lysed erythrocytes by adding distilled water to them. The supernatant liquid is treated with a bacteriocidical agent and lyophilized. Before use, more water must be added to the standard in order to reconstitute the initial solution. Such a standard is described in GB 1129873 A, for example.

The disadvantage of these standards is their limited storage life and, in the instance of lyophilized standards, the expense and inconvenience of handling and potential mistakes involved therein.

In JP 1-301166 a standard liquid for calibration of a hemocytometer is disclosed which includes substantially spherical, first and second particles in aqueous electrolyte solution. The particles have sulfonic acid groups and/or sulfonate groups on the surface. The first particles have an average size of 1.9 to 3 $\mu$m, and preferably 2 to 2.9 $\mu$m, which corresponds to the size of human blood platelets, while the second particles have diameters of 4.5 to 5.5 $\mu$m and correspond to erythrocytes in size. Via the known number of particles per unit volume of the standard liquid, the particle counter may be calibrated with respect to the number of erythrocytes, blood platelets, etc., to be determined. The particles are obtained, for instance, by polymerization from a vinyl monomer with sulfonic acid groups, or by copolymerizing the monomer with other monomers. The electrolyte solution contains sodium chloride, potassium chloride, sodium phosphate, for example. The ratio of the numbers of first and second particles is 1:10–40. The standard liquid may be dyed to permit its use as a standard for measuring hemoglobin in blood.

In U.S. Pat. No. 4,945,062, finally, a liquid control standard for use in the quality assurance of blood analysis instrumentation systems is disclosed. The control liquid is suitable for systems determining pH, $PCO_2$, and $PO_2$ in blood samples. The liquid is further used as a control standard for ion-selective electrodes (ISE), especially for measuring ionized calcium, total calcium, as well as the concentrations of Na, K and Li ions in blood samples. For measurement of the hemoglobin concentration (tHb) and several hemoglobin fractions, the autoclavable, stable, homogeneous standard contains absorbance means, preferably dyes from the group consisting of Acid Red Dye, Ponceau 3R Red Dye, Acid Yellow Dye, and Acid Blue Dye.

The above standards suffer from the disadvantage that the particles tend to sediment, such that the standards must be shaken or homogenized before use, or that some of the added dyes are not compatible with the sensitive layers of sensors and electrodes in the measuring devices and may thus obscure the measured values. Moreover, particle-sensitive measuring equipment will not respond to the dyes added.

SUMMARY OF THE INVENTION

It is an object of the present invention to propose a control or calibration standard for measuring instruments for optical determination of the hemoglobin concentration, which is suitable for use in systems with optical sensors, and which should be easy to handle and to prepare.

In the invention this object is achieved by providing that the scattering particles have a mean diameter of <0.6 $\mu$m, and preferably about 0.3 $\mu$m, and a volume concentration <1%, and preferably <0.3%. It has been found unexpectedly that the use of particles of a mean diameter of <0.6 $\mu$m, in particular in scattered-light geometries, will lead to reproducible measured values suitable for calibration and quality control in measuring instruments for optical determination of the hemoglobin concentration. Due to the small particle size, the scattering particles are kept in suspension more or less permanently by thermal molecular movement. It is not necessary in this context to modify the particles or their surfaces. The standard will thus remain homogeneous without any further measures and will be fully compatible with optical systems and sensors. Such scattering particles may also yield an optical signal which can be used for quality control or calibration of the oxygen saturation ($SO_2$%).

Scattering particles having the required properties are manufactured and supplied in various diameters and materials, for example by PROLABO, 45300 Pithiviers, France; BANGS LABS, Fishers, IN 46038, U.S.A.; DYNO PARTICLES AS, N-2001 Lillestrom, Norway; or POLYSCIENCES INC., Warrington, Pa. 1876, U.S.A.

According to the invention, the scattering particles may consist of substantially spherical beads made of polystyrene, polyvinyl toluene, styrene butadiene copolymers, polydivinyl benzene, polyolefin, polymethyl methacrylate, polyacrylate (acrylics), or latex. The mass density of the beads being substantially adjustable to that of the electrolyte solution. As the particle sedimentation rate will depend not only on particle diameter (square dependency), but also on the difference in density between particles and carrier liquid, particularly stable solutions may be obtained by matching the density of the electrolyte solution with that of the polymer used for the beads.

To increase oxygen solubility and match the density of the electrolyte solution with that of the particles, the control or calibration standard may contain water-soluble polymers, especially polyvinyl alcohol (PVA), polyvinyl pyrrolidone (PVP), or polyethylene glycol (PEG), or polyvalent alcohols, especially glycerol, propylene glycol or ethylene glycol, in concentrations of up to 90 percent by volume. The use of soluble polymers in control liquids for blood gas analyzers is described in U.S. Pat. No. 4,945,062, for instance. The present invention would permit the concentrations cited in the above publication to be exceeded, however. Oxygen solubility, for example, may be significantly increased by the addition of >5% vol (preferably >10% vol) of the above polymers, which in turn will improve the stability of the liquids. In addition to the above polymers it would also be possible to use monomers, i.e., preferably polyvalent alcohols, such as glycerol or ethylene glycol, in order to increase oxygen solubility. Concentrations of >50% vol may be used, above all, in blood gas control liquids. The concentration maximum will depend on the handling properties of the solutions, which are usually determined by the liquid's viscosity at high percentages of additives. For example, 90% ethylene glycol in water has a viscosity of 14 cp (at 20° C.); solutions of this kind are still considered usable.

The common feature of all these solutions is that their density is increased to values of 1.000 (water) to 1.11 g/ml (90% ethylene glycol in water), whereas electrolyte and buffer contents in the interesting range will exert a lesser influence on the density of the standard (0.015 g/ml at most).

Since scattering particles are commercially available in materials of different densities, the density of solution and particles may be adjusted by using the particle materials best suited for the purpose on hand. Precise adjustments may be made by varying the content of soluble polymers or polyvalent monomer alcohols.

In further development of the invention, a radiation absorber for wavelengths in the 600–1,200 nm range may be provided on the surface or in the interior of the scattering particles. Such absorbers include IR-absorbers of EXCITON, INC., P.O. Box 31126, Dayton, Ohio 45437-0126, IRA 980, IRA 866 and IRA 850, for example. IRA 980 Tris[4-(diethylamino)phenyl]-ammoniumylhexafluoroantimonate(1-) is a hydrophobic, water-insoluble dye which can be incorporated into the beads. The same applies to IRA 866 and IRA 850, which are equally well suited for incorporation into the beads. IRA 866 and 850 are more hydrophobic than IRA 980. By the addition of an absorber, the absorbance spectrum of the standard for different wavelengths may be better adjusted to that of a blood sample with different hemoglobin concentrations or oxygen saturations.

Furthermore, it is possible to use dyed beads (e.g., as supplied by BANGS LABS, Fishers, Ind. 46038, U.S.A.) with maximum absorptions at 643, 740 and 830 nm. Such dyed beads are especially well suited for standards which are used for calibration or quality control of the oxygen saturation. By binding the dye to the surface or interior of the beads, any degradation of the optical sensors of the devices to be calibrated can be avoided.

To prevent aggregation of the particles during long term static storage, it is proposed by the invention that the control or calibration standard contain a surfactant, i.e., preferably a non-ionic surfactant from the group of polyoxyethylene alkyl ethers, and preferably a polyoxyethylene hexadecylic ether (e.g. Brij-58), or an alkylphenyl-polyoxyethylene ether, and preferably an octylphenyl-polyoxyethylene ether (e.g., TritonX-100).

In addition to the systems measuring hemoglobin concentration and oxygen saturation many blood analysis instruments or systems include sensors for determination of the blood gas parameters (pH, $PCO_2$, $PO_2$) as well as sensors for measuring different ionic concentrations (e.g., Na, K, Ca, Mg, Cl). In accordance with the invention, the above described control and calibration standards are also suited for quality control and calibration of such instruments, if the electrolyte solution has a buffer providing a pH of 6.7 to 7.9, and preferably 7.1 to 7.7, and the values for $PCO_2$ are between 10 and 100 mmHg, and preferably between 20 and 80 mmHg, and for $PO_2$ between 15 and 400 mmHg, and preferably between 45 and 160 mmHg.

It is further provided that the electrolyte solution contains $Ca^{2+}$, $Na^+$, $K^+$, $Mg^{2+}$ and $Cl^-$ ions at concentrations corresponding to the ionic concentrations found in the blood.

It is proposed in the invention that the standard contain a Good's buffer as a buffer material, i.e., preferably HEPES, MOPS, or TES.

The standard of the invention may be supplied as a series of three solutions, Level 1 featuring low concentration values for the individual parameters, Level 2 normal values and Level 3 high values. In particular, the three solutions may have the following composition:

|         |          | Level 1 RANGE |        | Level 2 RANGE |        | Level 3 RANGE |        |
|---------|----------|---------------|--------|---------------|--------|---------------|--------|
| ANALYTE | UNITS    | MEAN VALUES   | +/−VAR | MEAN VALUES   | +/−VAR | MEAN VALUES   | +/−VAR |
| pH      | pH units | 7.14–7.20     | 0.003  | 7.40–7.44     | 0.003  | 7.58–7.64     | 0.003  |
| $PCO_2$ | mmHg     | 65–75         | 0.75   | 40–46         | 0.50   | 20–28         | 0.50   |
| $PO_2$  | mmHg     | 65–75         | 1.5    | 101–111       | 1.5    | 130–150       | 1.7    |
| $Na^+$  | mmol/L   | 115–125       | 1.5    | 135–145       | 1.5    | 150–180       | 1.5    |
| $K^+$   | mmol/L   | 2.5–3.5       | 0.09   | 4.5–5.5       | 0.09   | 5.5–6.5       | 0.09   |
| $Cl^-$  | mmol/L   | 81–91         | 1.0    | 98–108        | 1.0    | 116–126       | 1.0    |
| $Ca^{2+}$ | mmol/L | 1.3–1.5       | 0.05   | 1.05–1.25     | 0.05   | 0.6–0.8       | 0.05   |
| beads   | vol %    | 0.008–0.012   | 0.001  | 0.04–0.08     | 0.005  | 0.13–0.17     | 0.01   |

The bead concentrations cited in the above table for levels 1 to 3 of the standard liquid have yielded the following values for hemoglobin content (tHb) and oxygen saturation ($SO_2$) in a blood gas analyzer (OPTI CCA of AVL MEDICAL INSTRUMENTS AG, Schaffhausen CH):
Level 1: tHb=16–19 g/dl±1 g/dl; $SO_2$=80–86%±1.5%
Level 2: tHb=12–15 g/dl±1 g/dl; $SO_2$=88–94%±1.5%
Level 3: tHb=8–11 g/dl±1 g/dl; $SO_2$=94–100%±1.5%.
To obtain the above hemoglobin concentrations and $SO_2$ values, it is proposed that the scattering particles be non-functionalized polystyrene beads of a diameter of 0.3 μm. The polystyrene beads have a density of 1.050 g/ml and are supplied in aqueous suspension containing 10% solids by BANGS LABS, 9025 Fishers, Ind. 46038, U.S.A.

In accordance with the invention a preservative from the group of isothiazolinones, such as Proclin 300 or Mergal K9N may be added to the control or calibration standard. The active substances contained therein are 5-chloro-2-methyl-2H-isothiazole-3-one and 2-methyl-2H-isothiazole-3-one.

The standard is placed in ampoules at minimum quantities of about 1.7 ml.

An example of a standard solution formulated as proposed by the invention and comprising a series of three solutions is given below:

|  | Unit | Level 1 | Level 2 | Level 3 |
|---|---|---|---|---|
| HEPES (free acid) | mmol/L | 42 | 42 | 42 |
| NaOH | mmol/L | 30 | 30 | 30 |
| NaCl | mmol/L | 77 | 93 | 112 |
| NaHCO$_3$ | mmol/L | 12 | 19 | 22 |
| KCl | mmol/L | 3.0 | 5.0 | 6.0 |
| CaCl$_2$ | mmol/L | 1.6 | 1.35 | 0.8 |
| MgCl$_2$ | mmol/L | 1.2 | 0.75 | 0.4 |
| Proclin 300 | g/L | 0.2 | 0.2 | 0.2 |
| Beads (10% in water) | ml/L | 1.0 | 5.0 | 15.0 |
| Brij-58 | g/L | 0.05 | 0.05 | 0.05 |
| Gas treatment (37° C.) |  | Gas A | Gas B | Gas C |

The addition of gases takes place at 37° C. and is continued until the following equilibria are reached:
$PO_2(gas)=PO_2(liquid)$ and $PCO_2(gas)=PCO_2(liquid)$
Gas compositions:
Gas A: 10% (vol) $CO_2$, 10% (vol) $O_2$, balance $N_2$
Gas B: 5.5% (vol) $CO_2$, 15% (vol) $O_2$, balance $N_2$
Gas C: 3.5% (vol) $Co_2$, 20% (vol) $O_2$, balance $N_2$

We claim:

1. A control or calibration standard for use with instruments for optical measurement of hemoglobin concentration in blood samples, said standard being comprised of scattering calibration particles dispersed in an aqueous electrolyte solution, wherein said dispersed particles have a mean diameter of <0.06 µm and a volume concentration <0.3%, the mass density of said electrolyte solution substantially corresponding to a mass density of said scattering particles.

2. A control or calibration standard as claimed in claim 1, wherein said scattering particles consist of substantially spherical particles made of a polymer from the group consisting of polystyrene, polyvinyl toluene, styrene butadiene copolymers, polydivinyl benzene, polyolefin, polymethyl methacrylate, polyacrylate and latex.

3. A control or calibration standard as claimed in claim 1, wherein a radiation absorber for wavelengths in a 600–1200 nm range is provided on the surface or in the interior of said scattering particles.

4. A control or calibration standard as claimed in claim 1, wherein said electrolyte solution contains water-soluble polymers from the group consisting of polyvinyl alcohol (PVA), polyvinyl pyrrolidone (PVP), polyethylene glycol (PEG), and polyvalent alcohols, in concentrations of up to 90 percent by volume.

5. A control or calibration standard as claimed in claim 4, wherein said polyvalent alcohol is at least one alcohol selected from the group consisting of glycerol, propylene glycol and ethylene glycol.

6. A control or calibration standard as claimed in claim 1, wherein said standard additionally contains a surfactant.

7. A control or calibration standard as claimed in claim 6, wherein said surfactant is a non-ionic tenside selected from the group consisting of polyoxyethylene alkyl ether and alkylphenyl polyoxyethylene ether.

8. A control or calibration standard according to claim 7, wherein said polyoxyethylene alkyl ether is polyoxyethylene hexadecylic ether.

9. A control or calibration standard according to claim 7, wherein said alkylphenyl polyoxyethylene ether is octylphenyl polyoxyethylene ether.

10. A control or calibration standard as claimed in claim 1, wherein said scattering particles have a mean diameter of about 0.3 µm and a volume concentration of <0.3%.

11. A control or calibration standard for use with blood gas measuring systems and instruments for optical measurement of hemoglobin concentration in blood samples, said standard comprising scattering particles dispersed in an aqueous electrolyte solution, wherein said scattering particles have a mean diameter of <0.6 µm and a volume concentration of <0.3%, wherein said electrolyte solution contains a buffer providing a pH of 6.7 to 7.9 and wherein values for $PCO_2$ are between 10 and 100 mm Hg, and for $PO_2$ are between 15 and 400 mm Hg.

12. A control or calibration standard as claimed in claim 11, wherein said electrolyte solution contains at least one ion selected from the group of a group consisting of $Ca^{2+}$, $Na^+$, $K^+$, $Mg^{2+}$ and $Cl^-$ at concentrations corresponding to ion concentrations found in human blood.

13. A control or calibration standard as claimed in claim 11, wherein said standard contains a Good's buffer as said buffer.

14. A control or calibration standard according to claim 13, wherein said Good's buffer is selected from the group consisting of HEPES, MOPS and TES.

15. A control or calibration standard as claimed in claim 11, wherein said standard comprises a series of three solutions (Level 1, Level 2, Level 3) of the following compositions:

|  |  | Level 1 RANGE | | Level 2 RANGE | | Level 3 RANGE | |
|---|---|---|---|---|---|---|---|
| ANALYTE | UNITS | MEAN VALUES | +/−VAR | MEAN VALUES | +/−VAR | MEAN VALUES | +/−VAR |
| pH | pH units | 7.14–7.20 | 0.003 | 7.40–7.44 | 0.003 | 7.58–7.64 | 0.003 |
| PCO$_2$ | mmHg | 65–75 | 0.75 | 40–46 | 0.50 | 20–28 | 0.50 |
| PO$_2$ | mmHg | 65–75 | 1.5 | 101–111 | 1.5 | 130–150 | 1.7 |
| Na$^+$ | mmol/L | 115–125 | 1.5 | 135–145 | 1.5 | 150–180 | 1.5 |
| K$^+$ | mmol/L | 2.5–3.5 | 0.09 | 4.5–5.5 | 0.09 | 5.5–6.5 | 0.09 |
| Cl$^-$ | mmol/L | 81–91 | 1.0 | 98–108 | 1.0 | 116–126 | 1.0 |
| Ca$^{2+}$ | mmol/L | 1.3–1.5 | 0.05 | 1.05–1.25 | 0.05 | 0.6–0.8 | 0.05 |
| beads | Vol % | 0.008–0.012 | 0.001 | 0.04–0.08 | 0.005 | 0.13–0.17 | 0.01 |

16. A control or calibration standard as claimed in claim 15, wherein said scattering particles are non-functionalized polystyrene beads of a diameter of about 0.3 µm.

17. A control or calibration standard as claimed in claim 11, wherein said standard contains a preservative.

18. A control or calibration standard as claimed in claim 11, wherein said scattering particles consist of substantially spherical particles made of a polymer selected from the group consisting of polystyrene, polyvinyl toluene, styrene butadiene copolymers, polydivinyl benzene, polyolefin, polymethyl methacrylate, polyacrylate and latex.

19. A control or calibration standard as claimed in claim 11, wherein a mass density of said electrolyte solution substantially corresponds to a mass density of said scattering particles.

20. A control or calibration standard as claimed in claim 19, wherein said electrolyte solution contains water-soluble polymers selected from the group consisting of polyvinyl alcohol (PVA), polyvinyl pyrrolidone (PVP), polyethylene glycol (PEG), and polyvalent alcohols, in concentrations of up to 90 percent by volume.

21. A control or calibration standard as claimed in claim 20, wherein said polyvalent alcohol is at least one alcohol selected from the group consisting of glycerol, propylene glycol and ethylene glycol.

22. A control or calibration standard as claimed in claim 11, wherein said standard additionally contains a surfactant.

23. A control or calibration standard according to claim 11, wherein said pH is between 7.1 and 7.7.

24. A control or calibration standard according to claim 11, wherein said $PCO_2$ value is between 20 and 80 mmHg.

25. A control or calibration standard according to claim 11, wherein said $PO_2$ value is between 45 and 160 mmHg.

* * * * *